(12) United States Patent
Sherman et al.

(10) Patent No.: US 7,444,179 B2
(45) Date of Patent: Oct. 28, 2008

(54) DEVICES, SYSTEMS AND METHODS FOR CHARACTERIZATION OF VENTRICULAR FIBRILLATION AND FOR TREATMENT OF VENTRICULAR FIBRILLATION

(75) Inventors: Lawrence D Sherman, Pittsburgh, PA (US); Clifton W Callaway, Pittsburgh, PA (US); James J. Menegazzi, Pittsburgh, PA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 10/834,412

(22) Filed: Apr. 29, 2004

(65) Prior Publication Data

US 2004/0220489 A1 Nov. 4, 2004

Related U.S. Application Data

(60) Provisional application No. 60/466,361, filed on Apr. 29, 2003.

(51) Int. Cl.
*A61B 5/046* (2006.01)
(52) U.S. Cl. ............... 600/518; 607/5; 600/512; 600/515; 600/523; 128/920
(58) Field of Classification Search ............... 600/518, 600/523, 512, 515; 128/920; 607/5, 4
See application file for complete search history.

(56) References Cited

U.S. PATENT DOCUMENTS 5,077,667 A 12/1991 Brown
5,201,321 A * 4/1993 Fulton ............... 600/515
5,351,696 A * 10/1994 Riff et al. ............... 600/515
5,439,483 A 8/1995 Doung-Van (Continued)

FOREIGN PATENT DOCUMENTS

WO WO 01/17419 A1 3/2001

OTHER PUBLICATIONS

Sherman, L.D., et al. "Angular Velocity of Phase-space Trajectory Quantifies Change in Ventricular Fibrillation over Time." Academic Emergency Medicine 10(5)(May 2003): 504.*

(Continued)

*Primary Examiner*—Carl H. Layno
*Assistant Examiner*—Deborah Malamud
(74) *Attorney, Agent, or Firm*—Bartony & Hare, LLP

(57) ABSTRACT

A method of determining a state of ventricular fibrillation, includes: measuring the rhythm of the heart during ventricular fibrillation for a period of time; creating a lagged phase space reconstruction of the measured rhythm; determining a first value related to the rate of change of the leading edge of the phase space reconstruction over the period of time; and determining the state of ventricular fibrillation by relating the first value to the state of ventricular fibrillation. A defibrillation system includes at least one processor in communication with a sensor to measure heart rhythm and an applicator to apply a defibrillation pulse. The processor is adapted to create a lagged phase space reconstruction of ventricular fibrillation heart rhythm and to determine a first value related to the rate of change of the leading edge of the phase space reconstruction over a period of time.

21 Claims, 13 Drawing Sheets

U.S. PATENT DOCUMENTS

| | | | | |
|---|---|---|---|---|
| 5,471,991 | A | * | 12/1995 | Shinnar ............... 600/518 |
| 5,555,889 | A | * | 9/1996 | Karagueuzian et al. ..... 600/518 |
| 5,571,142 | A | | 11/1996 | Brown |
| 5,593,427 | A | | 1/1997 | Gliner |
| 5,643,325 | A | | 7/1997 | Karagueuzian |
| 5,645,070 | A | * | 7/1997 | Turcott ................ 600/515 |
| 5,676,690 | A | | 10/1997 | Noren |
| 5,683,424 | A | | 11/1997 | Brown et al. |
| 5,803,084 | A | * | 9/1998 | Olson ................. 600/512 |
| 5,957,856 | A | | 9/1999 | Weil |
| 6,144,877 | A | | 11/2000 | DePetrillo |
| 6,171,257 | B1 | | 1/2001 | Weil |
| 6,266,561 | B1 | | 7/2001 | Gliner |
| 6,347,248 | B1 | | 2/2002 | Gliner |
| 6,438,419 | B1 | * | 8/2002 | Callaway et al. ............ 607/5 |
| 6,442,421 | B1 | * | 8/2002 | Le Van Quyen et al. .... 600/544 |
| 6,490,478 | B1 | * | 12/2002 | Zhang et al. ............ 600/518 |
| 6,639,381 | B2 | | 10/2003 | Tamura et al. |
| 6,651,025 | B1 | * | 11/2003 | Drepper ............... 702/127 |
| 6,662,046 | B2 | | 12/2003 | Hansen |
| 6,671,547 | B2 | | 12/2003 | Lyster |
| 6,697,671 | B1 | | 2/2004 | Nova |
| 6,726,634 | B2 | | 4/2004 | Freeman |
| 2004/0215091 | A1 | * | 10/2004 | Lohman et al. ........... 600/515 |
| 2005/0171447 | A1 | * | 8/2005 | Esperer ................ 600/515 |

OTHER PUBLICATIONS

Sherman, L.D., et al. "Angular velocity: a new method to improve prediction of ventricular fibrillation duration." Resuscitation 60(1)(Jan. 2004): 79-90.*

Wang, H.E., et al. "Effects of biphasic vs monophasic defibrillation on the scaling exponent in a swine model of prolonged ventricular fibrillation." Academic Emergency Medicine 8(8)(Aug. 2001): 771-781.*

Lightfoot, CB; Hsieh, M, Callaway, CW, Fertig, KC, Sherman, LD, Menegazzi, JJ.; Dynamic nature of electrocardiographic waveform predicts rescue shock outcome in porcine ventricular fibrillation. Ann Emerg Med 2003, 230-241.

Sherman, Lawrence D. et. al. Angular Velocity: A New Method to Improve Prediction of Ventricular Fibrillation Duration, Resuscitation 2004; 60, 79-90.

Callaway CW, Sherman LD, Mosesso, VN, Holt E, Dietrich TJ, Clarkson, MC. ; Scaling exponent predicts defibrillation success for out-of-hospital ventricular fibrillation cardiac arrest. Circulation 2001; 103:1656-1661.

Hamprecht FA, Achleitner U, Krismer AC, Lindner KH, Wenzel V, et al. Fibrillation power, an alternative method of ECG spectral analysis for prediction of countershock success in a porcine model of ventricular fibrillation. Resuscitation. 2001;50:287-296.

Hamprecht FA, Jost D, Ruettimann M, Calamai F, Kowalski JJ.; Preliminary results on the prediction of countershock success with fibrillation power. Resuscitation: 2001;50:297-299.

Amann, A, Achleitner, U, Antretter, H; Bonati, Jo, Krismer, AC, Lindner, KH, et.al.; Analyzing ventricular fibrillation ECG signals and predicting defibrillation success during cardiopulmonary resuscitation employing N-(alpha)-histograms. Resuscitation 2001; 50:77-85.

Eftestol, T, Sunde, K, Aase, SO, Husoy, JH; Steen, PA.; 'Probability of successful defibrillation' as a monitor during CPR in ou-of-hospital cardiac arrested patients. Resuscitation 2001; 48:245-254.

Povoas, HP, Weil, MH, Tang, W, Bisera, J, Klouche, K, Barbatsis, A.; Predicting the success of defibrillation by electrocardiographic analysis. Resuscitation 2002; 53:77-82.

Menegazzi J.J.; Wang H.E.; et. al.; Immediate Defibrillation versus interventions first in a swine model of prolonged ventricular fibrillation. Resuscitation 2003; 59:261-270.

Lightfoot C.B.; Sorensen T.J.; et. al.; Physician interpretation and quantitative measures of electrocardiographic ventricular fibrillation waveform. Prehospital Emergency Care. Apr./Jun. 2001, vol. 5, No. 2: 147-154.

Goto Y.; Suzuki I.; Inaba H.; Frequency of ventricular fibrillation as predictor of one-year survival from out-of-hospital cardiac arrests. The American Journal of Cardiology, Aug. 15, 2003, vol. 92: 457-459.

Podbregar M.; Kovacic M.; et.al.; Predicting defibrillation success by 'generic' programming in patients with out-of-hospital cardiac arrest. Resuscitation 2003; 57: 153-159.

* cited by examiner

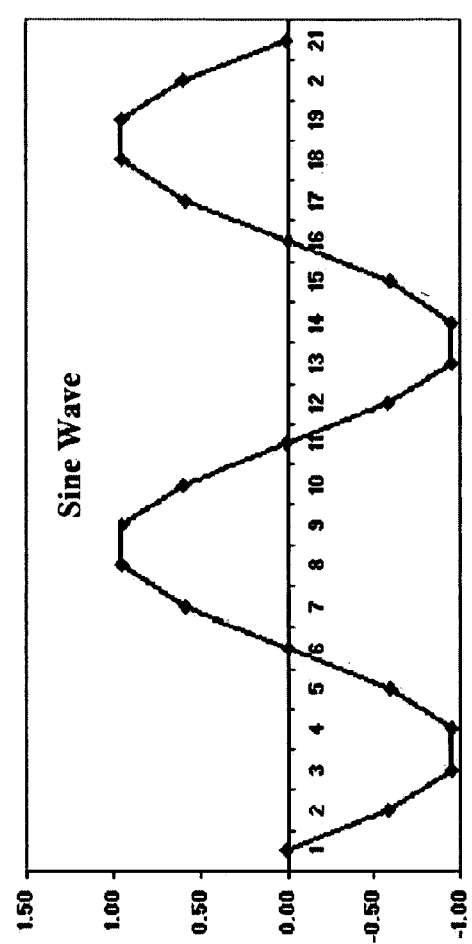
Fig. 1A
PRIOR ART
Fig. 1B
PRIOR ART
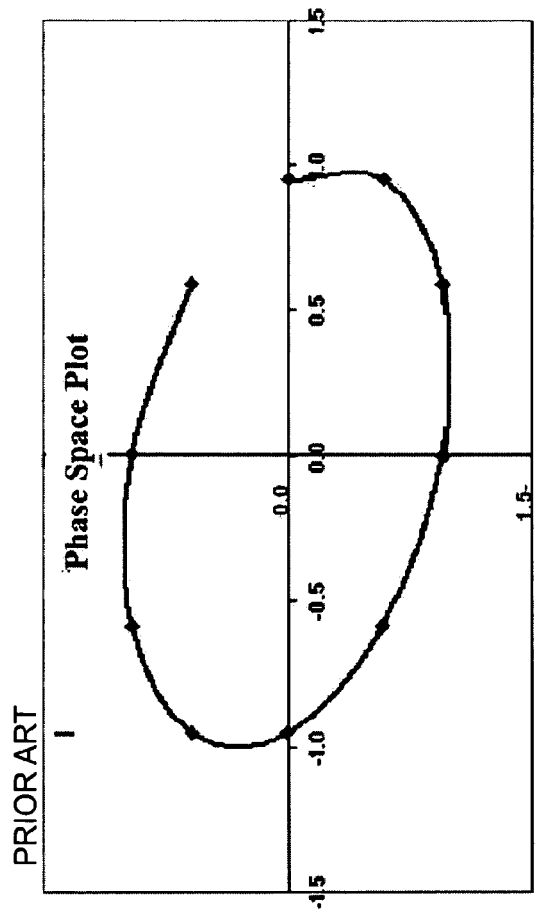
Fig. 1C
PRIOR ART

Fig. 9

| Test | Disease | | | |
|---|---|---|---|---|
| | VF < 5 min | VF > 5 min | | Positive Pred. Value<br>1850/2564<br>72% |
| VF < 5 min | 1850<br>(TP) | 714<br>(FP) | | |
| VF > 5 min | 197<br>(FN) | 2086<br>(TN) | | Negative Pred. Value<br>2086/2283<br>91.4% |
| | 2047<br>TOTAL < 5 min | 2800<br>TOTAL > 5 min | 4847<br>TOTAL of ALL | |
| | SENSITIVITY<br>1850/2047<br>90.4% | SPECIFICITY<br>2086/2800<br>74.5% | | Pretest Probability<br>2047/4847<br>42.2% |

DEVICES, SYSTEMS AND METHODS FOR CHARACTERIZATION OF VENTRICULAR FIBRILLATION AND FOR TREATMENT OF VENTRICULAR FIBRILLATION

CROSS-REFERENCE TO RELATED PATENT APPLICATION

This application claims the benefit of U.S. Provisional Patent Application Ser. No. 60/466,361, filed Apr. 29, 2003, the disclosure of which is incorporated herein by reference.

BACKGROUND OF THE INVENTION

The present invention relates to devices, systems and methods for the characterization of cardiac rhythm and, particularly, characterization of ventricular fibrillation, and to devices, systems and methods for use in the treatment of ventricular fibrillation based upon the characterization of ventricular fibrillation.

References set forth herein may facilitate understanding of the present invention or the background of the present invention. Inclusion of a reference herein, however, is not intended to and does not constitute an admission that the reference is available as prior art with respect to the present invention.

Ventricular fibrillation (VF) is a leading cause of sudden death. Indeed, ventricular fibrillation is the initial rhythm present in approximately 40% of non-traumatic sudden-death events. See Homberg, M, et al., "Incidence, duration and survival of ventricular fibrillation in out-of-hospital cardiac arrest patients in Sweden," *Resuscitation*, 44(1):7-17, 2000; and Cobb, L, et al., "Changing incidence of out-of-hospital ventricular fibrillation, 1980-2000," *JAMA*, 288(23):3008-13, 2000. Electrical defibrillation is the primary modality of treatment of ventricular fibrillation, but evidence is accumulating that its use in the phase or phases of VF generally associated the later time stages of VF, prior to providing ventilation, chest compressions and/or the administration of appropriate medication, is detrimental. Indeed, a number of studies have demonstrated that the probability of successful defibrillation is inversely related to the duration of VF and that immediate countershock was effective as initial therapy for the first several minutes only. See Yakaitis, R W, et al., "Influence of time and therapy on ventricular defibrillation in dogs," *Crit Care Med*, 8(3): 157-63, 1980.

The standard of care has been to provide immediate electrical countershock (defibrillation) to terminate the VF rhythm at the earliest possible time. The American Heart Association and the International Liaison Committee on Resuscitation have for many years recommended that three consecutive countershocks be delivered as the initial therapy when VF is present as the initial rhythm in cardiac arrest. See, for example, American Heart Association in Collaboration with the International Liaison Committee on Resuscitation, "Guidelines 2000 for Cardiopulmonary Resuscitation and Emergency Cardiovascular Care: an international consensus on science," *Circulation*, 102(8)(Suppl. I):I-136-57 2000 and American Heart Association in Collaboration with the International Liaison Committee on Resuscitation, "International Guidelines 2000 for CPR and ECC: a consensus on science," *Resuscitation*, 46(1-3): 1-447 2000.

That such therapy might not be optimum therapy in all cases was indicated in a study of CPR for 90 seconds prior to defibrillation. Cobb, L A, et al., "Influence of cardiopulmonary resuscitation prior to defibrillation in patients with out-of-hospital ventricular fibrillation," *JAMA*, 281(13):1182-8, 1999. That study demonstrated an increase in survival from 17 to 27% among patients given CPR prior to defibrillation when the response times were over four minutes. A subsequent study also supports those results. Wik, L, et al., "Delaying defibrillation to give basic cardiopulmonary resuscitation to patients with out-of-hospital ventricular fibrillation," *JAMA*, 289(11):1389-95, 2003. The results of that study indicated that when ambulance response times were over five minutes, survival to hospital discharge was 22% in patients who had CPR for three minutes prior to defibrillation as compared to 4% survival for those who had defibrillation as the first intervention.

It is a common clinical observation that early VF is "rough" or "coarse" in character or appearance and that it becomes more "smooth" or "fine" over time. Early efforts to quantify this quality and relate it to VF duration examined waveform amplitude as a measure of VF duration. Such attempts have met with only limited success however. See Weaver, W D, et al., "MK. Amplitude of ventricular fibrillation waveform and outcome after cardiac arrest" *Ann Intern Med*, 102(1):53-5 1985; and Hargarten, K M, et al., "Prehospital experience with coarse ventricular fibrillation: a ten year review," *Ann Emerg Med*, 19(2):157-62 1990. The limited success is believed to be a result of the variation in amplitudes measured arising from body habitus, electrode position, electrode conductance, myocardial mass, etc. A number of subsequent attempts have focused on examining the underlying average frequency composition of the waveform as derived from Fourier analysis. See Dzwonczyk, R, et al., "The median frequency of the ECG during ventricular fibrillation: its use in an algorithm for estimating the duration of cardiac arrest," *IEEE Trans Biomed Eng*, 37:640-6 1990; Brown, C G and Dzwonszyk, R, "Signal analysis of the human electrocardiogram during ventricular fibrillation: frequency and amplitude parameters as predictors of successful countershock," *Ann Emerg Med*, 27(2):184-8, 1996; Berg, R A, et al., "Precountershock cardiopulmonary resuscitation improves ventricular fibrillation median frequency and myocardial readiness for successful defibrillation from prolonged ventricular fibrillation: a randomized, controlled swine study," *Ann Emerg Med*, 40(6):563-70, 2002; U.S. Pat. Nos. 5,077,667, 5,957,856 and 6,171,255. While promising, such methods have not been fully developed for clinical use because, for example, the median frequency observed was multiphasic over time, leading to a broad range of time periods possible for a given observed median frequency. Moreover, like waveform amplitude, median frequency can be affected by body habitus, electrode position, electrode conductance, myocardial mass, etc.

Careful study of surface ECG waveforms during VF has led to the consideration that the apparently random activity may in fact be a manifestation of chaos. See, for example, Gray, R A, et al., "Spatial and temporal organization during cardiac fibrillation," *Nature*, 392:75-8 1998; Witkowski, F X, et al., "Spatiotemporal evolution of ventricular fibrillation," *Nature*, 392:78-82 1998; Witkowski, F X, et al., "Evidence for determinism in ventricular fibrillation," *Phys Rev Lett*, 75(6):1230-3, 1995; Garfinkel, A, et al., "Quasiperiodicity and chaos in cardiac fibrillation," *J Clin Invest*, 99(2):305-14, 1997; and Hastings, H M, et al., "Nonlinear dynamics in ventricular fibrillation," *Proc Natl Acad Sci USA*, 93:10495-9, 1996.

Borrowing from the fields of fractal geometry and nonlinear, chaotic dynamics, several studies addressed the problem of establishing the prior duration of VF in clinical and other settings through use of the scaling exponent (ScE). Callaway, C W, et al., "Scaling structure of electrocardiographic waveform during prolonged ventricular fibrillation in swine," *Pac-*

*ing Clin Electrophysiol,* 2:180-91, 2000; Sherman, L D, et al., "Ventricular fibrillation exhibits dynamical properties and self-similarity," *Resuscitation,* 47(2):163-73, 2000; and Lightfoot, et al., "Dynamic nature of electrocardiographic waveform predicts rescue shock outcome in porcine ventricular fibrillation," *Ann Emerg Med,* 42:230-241, 2003, the disclosure of which are incorporated herein by reference. The scaling exponent is a measure based on fractal geometry that measures the roughness of the VF waveform. It can be calculated in less than two seconds from a five-second surface recording of the ECG voltages. The scaling exponent has been found to increase over time from a low level of approximately 1.05 to a high level of 1.8 and provides a quantitative measure of the roughness of the VF waveform that is observed to change over time. The scaling exponent has also been shown to be predictive of the probability of successful defibrillation in patients treated with automated defibrillators. Callaway, C W, et al., "Scaling exponent predicts defibrillation success for out-of-hospital ventricular fibrillation cardiac arrest," *Circulation,* 103:1656-61, 2001; and U.S. Pat. No. 6,438,419, the disclosures of which are incorporated herein by reference. Recently, the scaling exponent was used to evaluate the effect of performing initial countershock versus starting resuscitation with CPR and/or medication prior to countershock. Menegazzi, J J, et al., "Immediate countershock after prolonged ventricular fibrillation is detrimental," *Circulation,* 106(19) (Suppl II):II-192 (abstract) 2002, the disclosure of which is incorporated herein by reference. Those studies have demonstrated that in prolonged VF (that is, VF in which the ScE has progressed to 1.3 or higher), providing CPR and drugs significantly increases survival. The converse of that observation is that defibrillating prior to other interventions in prolonged VF is detrimental and leads to a decrease in survival.

Although progress has been made in developing methods for characterizing ventricular fibrillation, it remains desirable to develop improved devices, systems and methods for characterizing ventricular fibrillation as well as improved treatment devices, systems, methods and protocols for treatment of ventricular fibrillation based thereon.

SUMMARY OF THE INVENTION

In general, the present invention provides new quantitative measures of the heart rhythm waveform and, particularly, the ventricular fibrillation waveform, related to the rate of change of the leading edge of a phase space reconstruction of the waveform (for example, the angular velocity and/or the angular area). The angular velocity and/or the angular area can be determined from a very short interval of ventricular fibrillation waveform. Indeed, 5-second intervals of ventricular fibrillation waveform were analyzed in the studies of the present invention.

In one aspect, the present invention provides a method of determining a state of ventricular fibrillation, including: measuring the rhythm of the heart during ventricular fibrillation for a period of time; creating a phase space reconstruction of the measured ventricular fibrillation heart rhythm; determining a first value related to the rate of change of the leading edge of the phase space reconstruction over the period of time; and determining the state of ventricular fibrillation by relating the first value to the state of ventricular fibrillation.

The first value can, for example be the average angular velocity for the period or the angular area for the period. The average angular velocity for the period of time can be calculated as the rate of rotation of the leading edge of the phase space reconstruction about the center of mass of points at an average rate. The phase space reconstruction can be a two-dimensional reconstruction or a three-dimensional reconstruction.

The method can further include determining a second value related to the fractal self-similarity dimension of the ventricular fibrillation heart rhythm for the period of time. In this embodiment, the step of determining the state of fibrillation includes the step of relating at least one of the first value and the second value to the state of fibrillation. The first value and the second value are preferably both related to the state of fibrillation. The second value can, be one of several values related to (and including) the fractal self-similarity dimension. For example, the first value can be the Hurst exponent or the scaling exponent. Several different numerical techniques for estimating these measures provide similar values. The most robust and numerically simplest algorithm for estimating the fractal self-similarity dimension is calculation of the scaling exponent.

Preferably, unfiltered waveform (ECG) output is used in calculating the scaling exponent as filtering the output can affect the value. However, such output filtering does not affect the rate of rotation of the leading edge of the phase space reconstruction and, thus, does not affect the angular velocity.

In one embodiment, the determined state of ventricular fibrillation is associated with a probability of success of a mode of treatment of ventricular fibrillation. The mode of treatment can, for example, be a defibrillation shock. The determination of the probability of success of a defibrillation shock can, for example, be related to both the angular velocity and the scaling exponent. The measure values (or one or more value derived therefrom) can, for example, be compared to stored or historical values of the variables or to the output of one or more algorithms derived from such values. Values other than the first value and the second value can also be determined. Moreover, the first and/or second values can be measured over multiple periods of time in determining the state of ventricular fibrillation.

In another aspect, the present invention provides a method of determining a treatment for a patient experiencing ventricular fibrillation, including: measuring the rhythm of the heart during ventricular fibrillation for a period of time; creating a phase space reconstruction of the measured ventricular fibrillation heart rhythm; determining a first value related to the rate of change of the leading edge of the phase space reconstruction over the period of time; and relating the first value to a treatment for the patient. As described above, the first value can, for example, be the average angular velocity for the period or angular area for the period. As also described above, the method can further include determining a second value related to the fractal self-similarity dimension of the ventricular fibrillation heart rhythm for the period of time. In that embodiment, the step of determining the treatment can include the step of relating at least one of the first value and the second value to the treatment. Once again, the second value can be the scaling exponent.

In a further aspect, the present invention provides a system for providing an indication of a state of ventricular fibrillation. The system includes at least one sensor to measure heart rhythm and at least one processor in communication with the sensor. The processor is adapted to create a phase space reconstruction of ventricular fibrillation heart rhythm measured over a period of time and to determine a first value related to the rate of change of the leading edge of the phase space reconstruction over the period of time. The system further includes a user interface system in operative connection with the processor. The user interface system is adapted to provide information related to the first value, for example, over multiple periods of time. The processor can be further adapted to determine a second value related to the fractal self-similarity dimension of the ventricular fibrillation heart rhythm for the period of time. In this embodiment the user interface system is adapted to provide information related to at least one of the first value and the second value.

In another aspect, the present invention provides a defibrillation system for use in treatment of ventricular fibrillation. The system includes at least one sensor to measure heart rhythm and at least one applicator to apply a defibrillation pulse to a patient (either a human or another member of the animal kingdom). The system further includes at least one processor in communication with the sensor and the applicator. The processor is adapted to create a phase space reconstruction of ventricular fibrillation heart rhythm measured over a period of time and to determine a first value related to the rate of change of the leading edge of the phase space reconstruction over the period of time. The system further includes a user interface system in operative connection with the processor to provide information related to rate of change to a user. The processor can further be adapted to determined a second value related to the fractal self-similarity dimension of the ventricular fibrillation heart rhythm for the period of time. In that embodiment, the user interface provides information related to at least one of the first value and the second value.

In another aspect, the present invention provides a method of creating a relation to characterize ventricular fibrillation including: measuring heart rhythm during ventricular fibrillation for an epoch comprising a period of time for a number of unique epochs; creating a phase space reconstruction of the measured ventricular fibrillation heart rhythm for each epoch; and determining a first value related to the rate of change of the leading edge of the phase space reconstruction for each epoch. Preferably, the unique epochs are sequential epochs. The unique epochs can, for example, be sequential epochs of approximately 5 seconds.

In still a further aspectt, the present invention provides a method of determining a state of a heart rhythm waveform, including: measuring the rhythm of the heart for a period of time; creating a phase space reconstruction of the measured heart rhythm waveform; determining a first value related to the rate of change of the leading edge of the phase space reconstruction over the period of time; and determining the state of the heart rhythm waveform by relating the first value to the state of the heart rhythm waveform.

The angular velocity and the angular area of the ventricular fibrillation waveform vary in a predictable manner over time during ventricular fibrillation and quickly provide a characterization of the ventricular fibrillation waveform that can be related to a "character", "phase" or "state" of ventricular fibrillation. In that regard, ventricular fibrillation appears to exhibit different states which can be associated with different preferred treatment protocols. Generally, such states of ventricular fibrillation can be related to the duration of ventricular fibrillation as untreated ventricular fibrillation appears to pass through various states throughout its duration. For example, as described above, the likelihood of successful defibrillation is determined, in significant part, by the duration of ventricular fibrillation, and a measure of ventricular fibrillation duration can serve as a way of estimating the likelihood of shock success. For this purpose, shock success can be defined as the restoration of a perfusing or organized cardiac electrical rhythm, or as the suppression of ventricular fibrillation, within a short period of time following the application of the defibrillation shock (usually within approximately a minute or shortly thereafter). Duration of ventricular fibrillation is not the only determinant of shock success, however. If, for example, cardiopulmonary resuscitation or CPR is applied for a period of time during ventricular fibrillation, the likelihood of shock success can be greater than if the patient did not receive CPR. Moreover, if ventricular fibrillation is triggered by a progressive ischemic event rather than a sudden electrical event, such ventricular fibrillation is more difficult to shock successfully for the same duration of ventricular fibrillation. The present inventors have discovered that certain values related to (or a measure of) the rate of change of a phase space reconstruction of the ventricular fibrillation waveform (such as the angular velocity and the angular area), particularly when used in conjunction with a value related to (or a measure of) the fractal self-similarity dimension of the waveform (such as the scaling exponent) seem to take any and all of the factors affecting the character or state of ventricular fibrillation into account, allowing, for example, a prediction of defibrillation shock success to be made without having to consider such individual factors.

The angular velocity, for example, exhibits a multiphasic pattern in which there is an initial increase prior to an eventual decline with time during ventricular fibrillation. In that regard, by constructing a flat, circular disk-shaped structure in a three-dimensional phase space and measuring the velocity of rotation of the position vector over time, the angular velocity rises from 58 radians/sec at 1 minute to 79 radians/sec at 4 minutes and then decreases in a generally linear manner to 32 radians/sec at 12.5 minutes. In several studies of the present invention, when the angular velocity (which took less than 2 seconds to calculate) was used in the present invention in conjunction with the scaling exponent to establish that less than 5 minutes of ventricular fibrillation had passed, over 90% of episodes of less than 5 minutes ventricular fibrillation were identified on the basis of a single 5-second recording of the waveform. As the appropriate treatment of ventricular fibrillation is strongly dependent upon the state of ventricular fibrillation (which, in turn, is often related to the duration thereof), the improved devices, systems and methods of the present invention, which provide an indication of the state of ventricular fibrillation from a short segment of recorded heart rhythm/ventricular fibrillation provide a significant improvement in the art.

BRIEF DESCRIPTION OF THE DRAWINGS

Other aspects of the invention and their advantages will be discerned from the following detailed description when read in connection with the accompanying drawings, in which:

FIG. 1A illustrates a table of the coordinates of the sine wave wherein the γ-coordinate points exhibit a lag of 3.

FIG. 1B illustrates a plot of the sine wave

FIG. 1C illustrates a phase space plot created from the data table of FIG. 1A.

FIG. 9 illustrates the sensitivity and specificity of the classification system of FIG. 8 as applied to the studies of the present invention.

DETAILED DESCRIPTION OF THE INVENTION

In the studies of the present invention, the ability of angular velocity/angular area (alone and in conjunction with the scaling component) to predict or determine a state, phase or class of VF as represented or modeled by the duration of VF was determined. In a number of the studies of the present invention, a classification system including two classes of VF (that is, a first class of less than 5 minutes duration for which defibrillation is likely to be successful and a second class of greater than 5 minutes duration for which defibrillation is unlikely to be successful) is described. As set forth above, a delineation based upon a VF duration of 5 minutes has been related to the success of a defibrillation shock. Although the methods, devices and systems of the present invention are discussed herein generally in terms of a classification system including two classes, a classification system having greater than two classes or a continuous characterization is readily set forth.

A characteristic of chaotic systems is that it is often possible to construct a geometric object in phase space from lagged copies of the time series. See, for example, Williams, G P, Chaos Theory Tamed, Washington, D.C., Joseph Henry Press, p. 353-71. 1997. The concept of phase space is derived from the study of wave phenomenon, such as the sine wave. When the values representing one copy of a sine wave are placed side by side with a second duplicate copy of the values of the sine wave and they are offset by a set number of values (called the "lag"), the two copies represented are said to be out of phase. By plotting the values of one copy (or phase) of the sine wave on the x-axis and the second copy with its differing phase on the y-axis, a phase space plot is formed. Referring to FIGS. 1A through 1C, each pair of values (see FIG. 1A) from the two copies then defines a point. When these points are plotted with the values in the first column used as the x-coordinate and the values in the second column used as the y-coordinate, an oval or circular structure results as shown in FIG. 1C. By varying the lag, the phase is varied. When an unknown series of values is evaluated by taking two copies (for two-dimensional plots) or three copies (three-dimensional plots) offset by a given lag, this method is termed "phase space reconstruction".

Figure 2A:
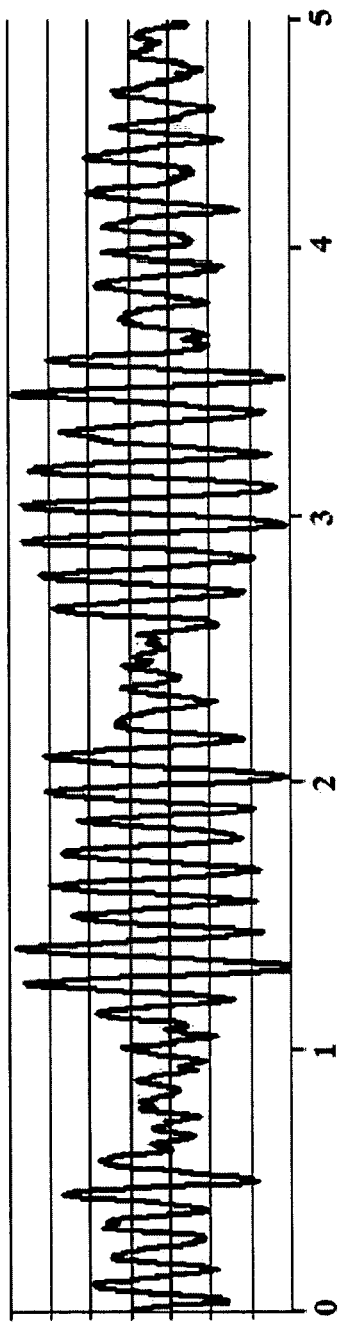
FIG. 2A illustrates a 5-second interval of heart rhythm during ventricular fibrillation.
Figure 2C:
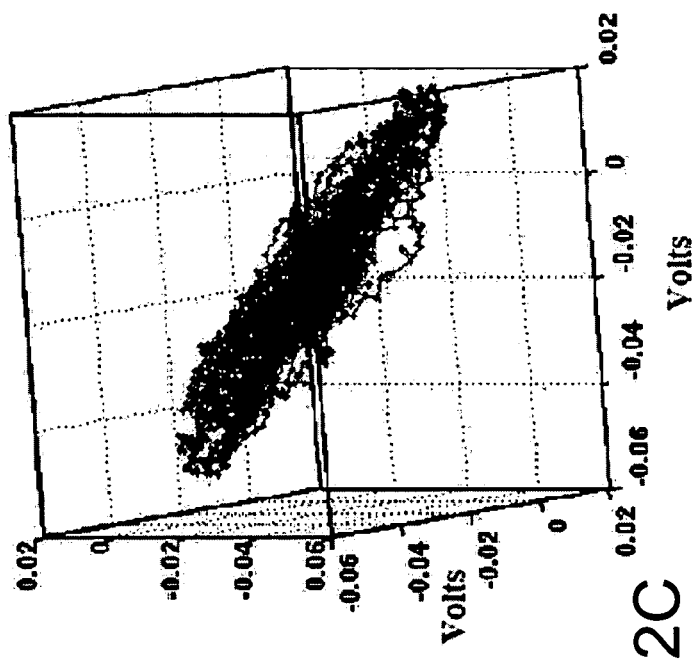
FIG. 2C illustrates the three-dimensional phase space reconstruction of FIG. 2B which has been rotated to illustrate the disk-shaped nature of the phase space reconstruction.
Figure 2B:
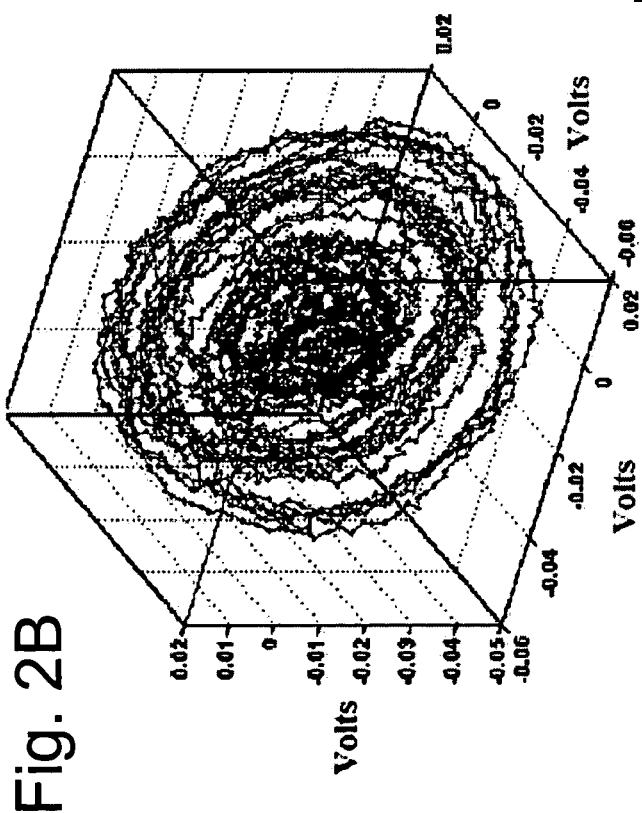
FIG. 2B illustrates a three-dimensional phase space reconstruction plot of the angular velocity of the heart rhythm of FIG. 2A
Figure 3:
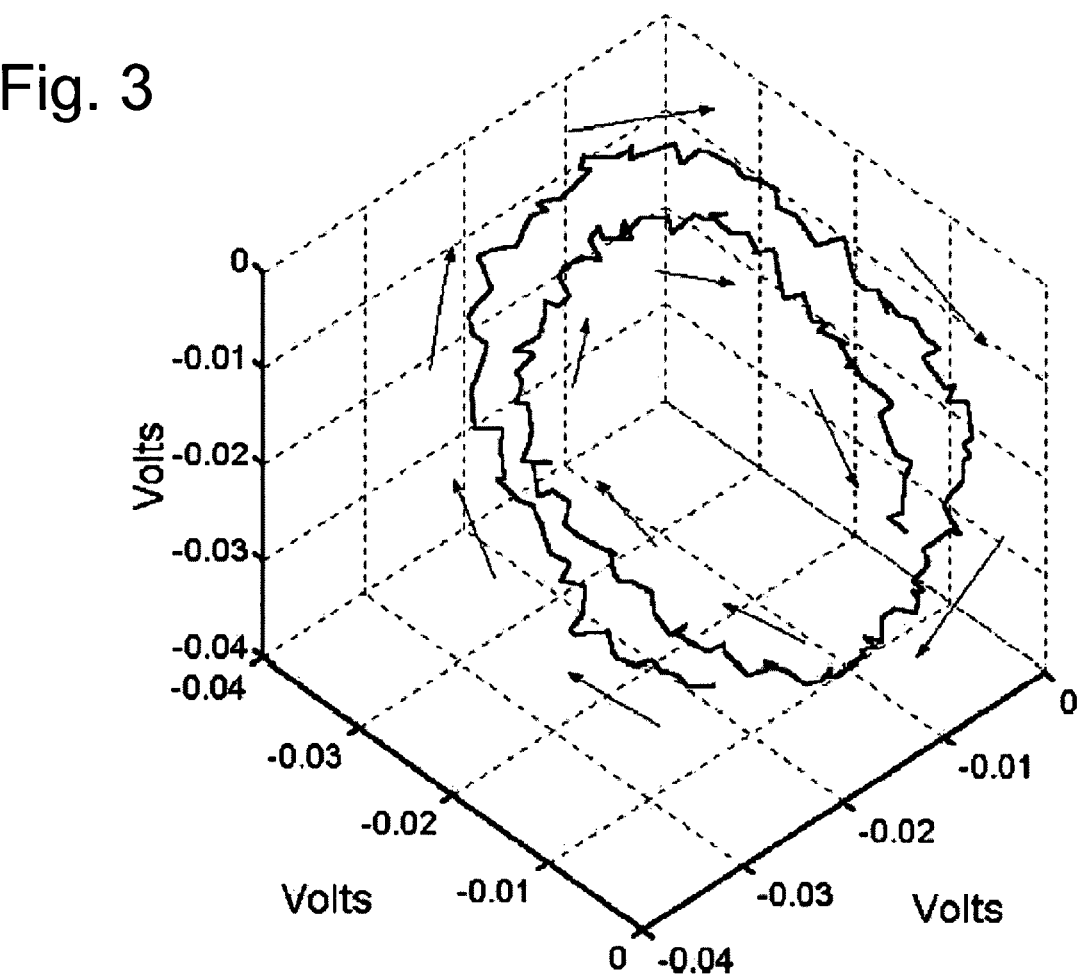
FIG. 3 illustrates the rotation of the leading edge of the phase space reconstruction of FIG. 2A.

For the VF time series, the phase reconstruction method produces an approximately circular trajectory of points formed in phase spaces of two or three dimensions, but noted to be planar and disk shaped when seen in three dimensions. A representative five second recording of VF from one experimental series is shown FIG. 2A, with the trajectories of points in three dimensions formed from this series shown both face on (FIG. 2B) and on edge (FIG. 2C) to demonstrate the disk-shaped structure formed. If one follows the formation of this structure as it is formed graphically point by point from the lagged pairs of points, it is noted that the leading edge rotates around the center (see FIG. 3). The rate of change or rate of rotation, termed the angular velocity (AV), has been found by the present inventors to undergo a gradual, characteristic decrease with time during VF. Furthermore, the angular area, which is the measure of the area swept out by the position vector as the leading edge is traced out over time, can also be used to characterize the state of VF. The angular area, which like the angular velocity is related to the rate of change of the leading edge of the phase space reconstruction, also incorporates the amplitude of the waveform, which can, for example, improve characterization of VF.

The velocity at which the leading edge of the trajectory traces out its path can be calculated in radians per second. The AV, alone or combined with the scaling exponent (ScE), as determined, for example, from a single 5-second recording of VF, allows an observer to predict the duration of VF (for example, whether the episode of VF being examined was from a time frame of less than five minutes VF duration or from a period of greater than five minutes total VF duration).

In several studies of the present invention, using recordings of up to 12.5 minutes of VF from 45 healthy swine, which were obtained prior to any other interventions, the AV method was set forth and compared to the ScE method. The relative strengths of the two methods were studied and subsequently combined in a two-dimensional scatter plot as described below. Probability density estimates based on this plot were used to establish objective criteria for separating VF of less than 5 minutes duration from the more prolonged VF.

In the studies of the present invention, (which were approved by the University of Pittsburgh Institutional Animal Care and Use Committee), seventy-two mixed-breed domestic swine of either sex were sedated with intramuscular ketamine (10 mg/kg) and xylazine (4 mg/kg) and then anesthetized with intravenous alpha-chloralose (40 mg/kg bolus followed by 10 mg/kg/hr drip). The swine were intubated with a 5.0 cuffed tracheal tube and ventilated with room air at a tidal volume of 15-20 $cm^3$/kg and a rate of 12-16 respirations/min. Eucapnia was assured and adjusted to between 35 and 45 mmHg by using end-tidal side stream carbon dioxide monitoring from a LifePak 12 monitor defibrillator (available from Medtronic Physio-Control Inc. of Redmond, Wash.). Neuromuscular paralysis was achieved with pancuronium (4 mg IV bolus, repeated 2 mg IV bolus as needed), and right femoral arterial and central venous catheters were placed in the descending aorta and right atrium with micro-manometer tipped pressure transducers for continuous recording. The electrocardiogram and arterial pressure tracings were continuously digitally recorded at a rate of 1000 points/sec using the Chart software package (version 3.6, available from AD Instruments of Castle Hill, Australia). Ventricular fibrillation was induced by a transthoracic 3 seconds, 60 Hz, 100 mA AC current.

The VF waveform obtained for analysis was then recorded from the animal as unfiltered lead-II signal via a wide bandpass preamplifier (Model DAM 50, available from World Precision Instruments of Sarasota, Fla.) with a 10-fold dc gain. The unfiltered signal was then sent through an SCC AI07 signal conditioning unit available from National Instruments in an SCC 2345 chassis (National Instruments), where it was amplified 200-fold and passed directly to a PC 6024E NI-DAQ data acquisition card (National Instruments). The leading edge of the trajectory in phase space (see FIG. 3) was traced out using a DELL® PENTIUM® 3 based computer. The signal was acquired at a rate of 1000 Hz in a double buffer of 10,000 points so that a 5000-point sample was taken into the buffer every 5 seconds. Using C++ code (Microsoft Visual C++ 6.0), the ScE was calculated, displayed and recorded in real time at 5 seconds intervals.

In all, 72 animals were involved in a protocol. The animals were placed in VF, which was allowed to continue until the animals reached ScE values (calculated in real time) of 1.1, 1.2, 1.3 or 1.4, before one of several interventions were applied and attempts at resuscitation were begun. The animal study protocol used in the studies of the present invention is described in detail in Menegazzi, J J, et al., "Immediate countershock after prolonged ventricular fibrillation is detrimental," *Circulation,* 106(19) (Suppl II):II-192 (abstract) 2002. A total of 45 swine were allowed to reach an ScE of 1.3 or 1.4. Swine in which the ScE was allowed to reach only 1.1 or 1.2 were in VF for less than 5 minutes and were not in VF for a sufficient length of time to be included in the study of VF duration of the present invention. Many of these recordings were of less than 60 seconds duration to reach an ScE of 1.1 and less than 3 minutes to reach an ScE of 1.2. No other inclusion or exclusion criteria were used. For statistical purposes it was made sure that there were a sufficient number of animals in whose case VF was recorded to 12.5 min or greater to allow analysis to the 12.5 min time period.

The recordings were analyzed for both the changes in scaling exponent over time (ScE) and the phase space reconstruction with calculation of the rotational velocity of the position vector over time (AV). These values were then analyzed as described below.

Scaling Exponent

As described above, the scaling exponent is a measure of the "roughness" of the VF waveform. It was derived from the fractal self-similarity dimension and its evaluation here is based on the method of Higuchi for time series data. See Higuchi, T., "Approach to an irregular time series on the basis of the fractal theory," *Physica D,* 31:277-83, 1988, the disclosure of which is incorporated herein by reference. The determination of the scaling exponent is described in detail in Callaway, C W, et al., "Scaling structure of electrocardiographic waveform during prolonged ventricular fibrillation in swine," *Pacing Clin Electrophysiol,* 2:180-91, 2000; Sherman, L D, et al., "Ventricular fibrillation exhibits dynamical properties and self-similarity," *Resuscitation,* 47(2):163-73, 2000 and U.S. Pat. No. 6,438,419, the disclosures of which are incorporated herein by reference.

Given a data set of length n, the sum of potential changes, L, of the segment was calculated for different sampling lags, k. The points are denoted by Yi, which is the ith measurement in the series. The sampling lag k was varied from 1 to 40. For each sampling lag, the distance or average difference separating the ith and (i+k)th points measured in the interval was calculated as $$\langle l(k) \rangle = \frac{1}{n-k} \sum_{i=1}^{n-k} |Y_i - Y_{i+k}|.$$

Here the symbol < > indicates the average value of l for a total of (n-k) measurements, using a separation of k units between points. The total potential difference for the entire data set at the lag of k, i.e. L(k), was then calculated as L(k)=<l(k)> (n/k). The L(k) thus calculated for the series at k values from 1 to 40 were then fitted to the exponential function:

$$L(k)=K^{1-d}$$

Taking the logarithms of this equation yields log L(k)=(1-d) log k.

By plotting log L(k) versus log k a curve is produced. If there is a linear portion, the slope of this line is (1-d). When there is "scaling" behavior a linear segment or plateau will be identified. In the analysis of VF waveforms all curves show a clear region of scaling, with a definite plateau. This plateau was identified using 10 points centered on the inflection point of the curve occurring between k=2 and k=40. The value of d was determined at this point from the slope of the line fitted by least-squares linear regression to a plot of log L(k) versus log k, such that d=1-slope. Conceptually, the ScE is a summary statistic which reflects how estimates of the total length L(k) varies with the sampling lag k. Lower values of ScE correspond to VF which appears "coarse" to the clinical observer, and higher values correspond to VF which appears "fine".

Figure 4:
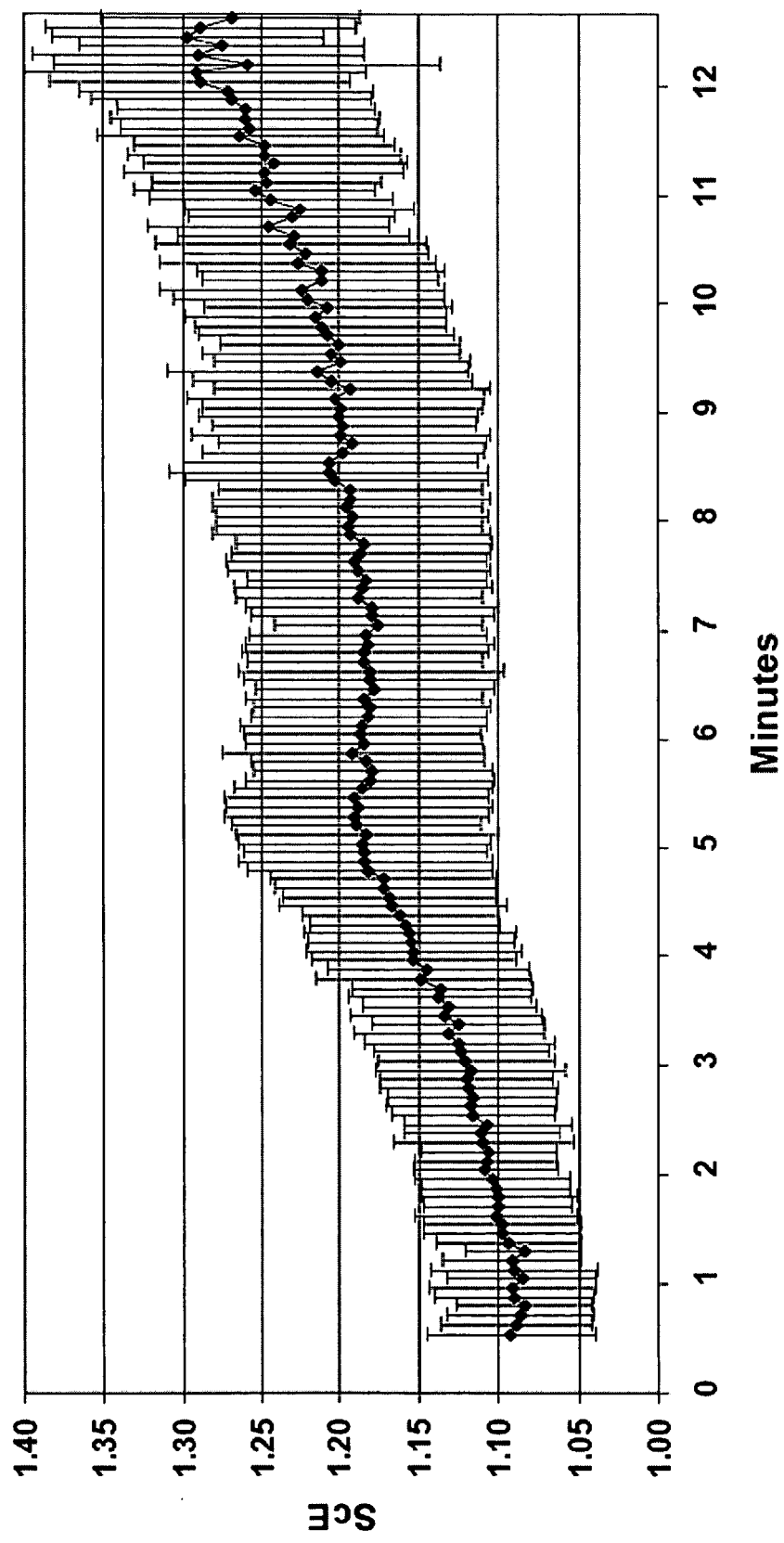
FIG. 4 illustrates a plot of the scaling exponent as a function of time during ventricular fibrillation.

Results of scaling exponents calculated for 45 swine over the 12.5 minute duration of VF are shown in FIG. 4. There was an increase in the ScE over the full interval. In the initial 5 minutes of VF, there was a rapid rise in the ScE. However, the middle portion of the ScE plot formed a plateau for approximately 3 minutes, from 5 to 8 minutes. After 8 minutes, the ScE increased through the remainder of the 12.5 minutes of VF duration. The standard deviation at each point was noted to be comparatively large after the first 4 minutes and in the plateau of the curve from 5 to 8 minutes. Thus, separation of time periods was difficult over that range of time. The initial rapid increase at times less than 5 minutes made the early portion of the curve useful when combined with the AV in a two-dimensional probability density analysis as described below.

Angular Velocity

The leading edge of the circular structure produced in the phase space reconstruction rotates about the center of mass of the points at an average rate in a 5 second interval. In preliminary investigations, this rate appeared to vary with the time period of VF from which the data were selected. It was therefore decided to investigate this phenomenon in a systematic manner. Computer programs written in C++ were used to calculate the average angular velocity of the leading edge of the trajectory over 5 second intervals taken consecutively during the course of VF. The trajectory was formed in the three-dimensional phase space by taking voltage measurements at a sampling rate of 1000 $\sec^{-1}$, for a total of 5000 points. Indexing the voltages for each interval as Yi, with $1 \leq i \leq 5000$, the points of the trajectory, (x, y, z), can be written as Ai=(Yi, Yi+k, Yi+2k), with i ranging over all points such that i+2k$\leq$5000, where k is the given lag. The trajectory was then centered about the origin by subtracting the mean of the points from each point. Each point Ai is then treated as a vector based at the origin.

As noted above, the trajectory is planar in three-dimensional phase space. However, the plane of the trajectory changes gradually over the time course of VF. Therefore, the plane was determined for each 5 second phase space reconstruction. The normal vector to the plane was calculated by taking the vector cross product of all temporally consecutive points in the trajectory, and then averaging. That is, the plane normal N=Ai×Ai+1 was averaged over all points in the trajectory. Positive rotation was defined as a counterclockwise progression about N (based on a positive cross product using the "right-hand rule").

The angular velocity of the trajectory was then calculated about the N vector, placed at the origin. The measure was defined as the average angular separation between consecutive points in the trajectory in relation to the plane normal, and it carries units of radians per point. At the 1000 points/second sampling rate, this is equivalent to radians per millisecond. The AV is then multiplied by $10^3$ and reported in radians per second. For all points Ai and Ai+1, and a plane normal N, the separation angle between Ai and Ai+1 was calculated as $$\theta = \cos^{-1}\left(\frac{A_i A_{i+1}}{|A||A_{i+1}|}\right).$$

Since the direction of rotation of the angular velocity was arbitrarily determined by whether the lagged vectors are formed as (Yi, Yi+k, Yi+2k) or (Yi, Yi-k, Yi-2k) it was determined that the absolute value of the angular velocity would be used, regardless of the direction of rotation. The rotation is clockwise or negative in all cases using the convention of (Yi, Yi+k, Yi+2k).

Figure 5:
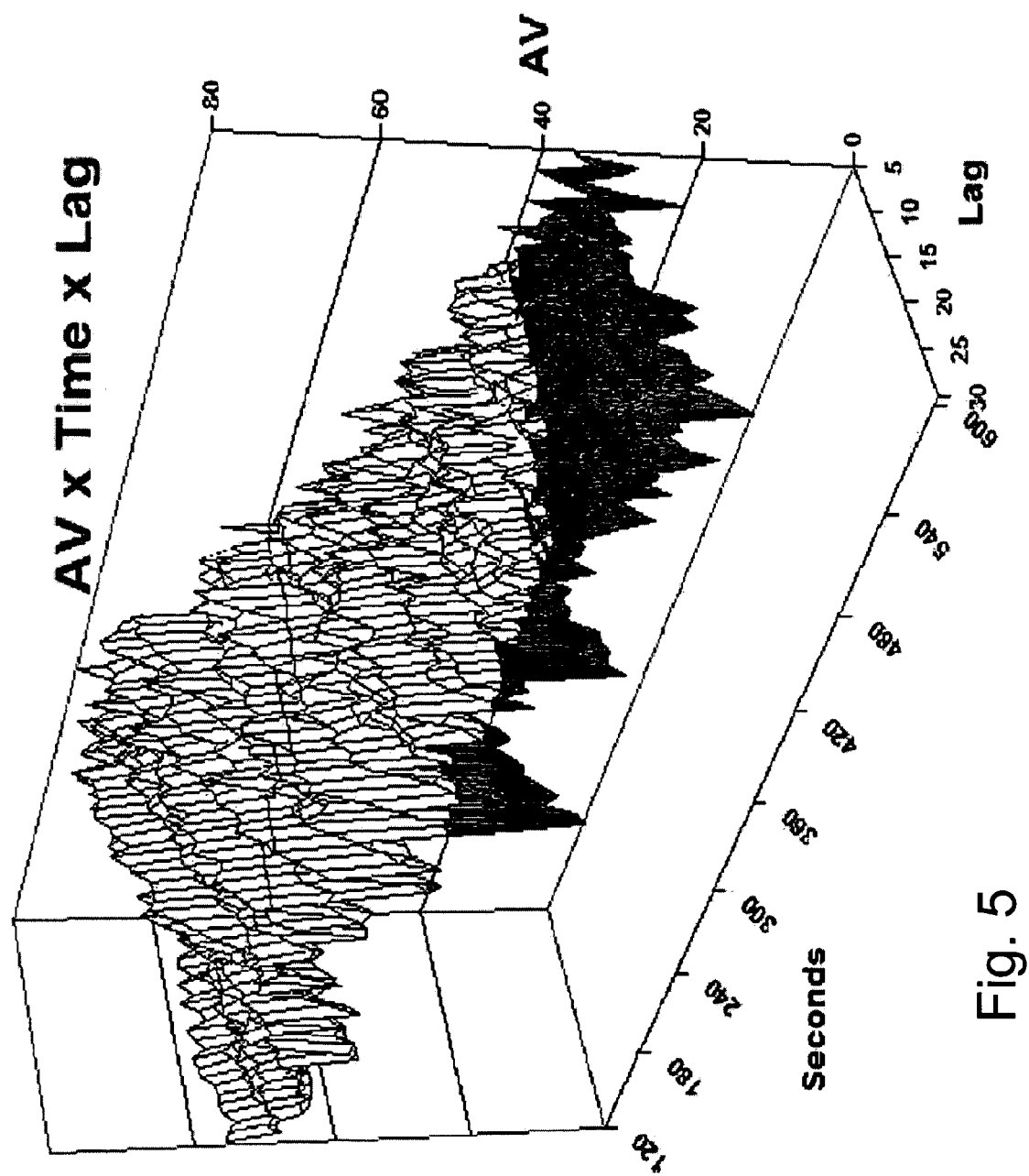
FIG. 5 illustrates a three-dimensional plot of the angular velocity as function of time over a range of lags.

Time series measurements were collected from 45 swine as described above from the initiation of VF to the first intervention. Initial evaluation involved reconstructing the trajectory in three dimensions with 5 second intervals of data. These 5000-point intervals were analyzed at "lags" varying from 5 to 30 to determine how the rate of rotation varied with lag (see FIG. 5). A lag of approximately 10 demonstrated the maximum vertical range of angular velocity over the 12.5 minutes. The AV remains relatively stable over lags of 5 to 15 so that the AV calculations were robust with respect to selection of lag. A lag of 10 was therefore chosen for all AV determinations in the studies of the present invention.

Figure 6:
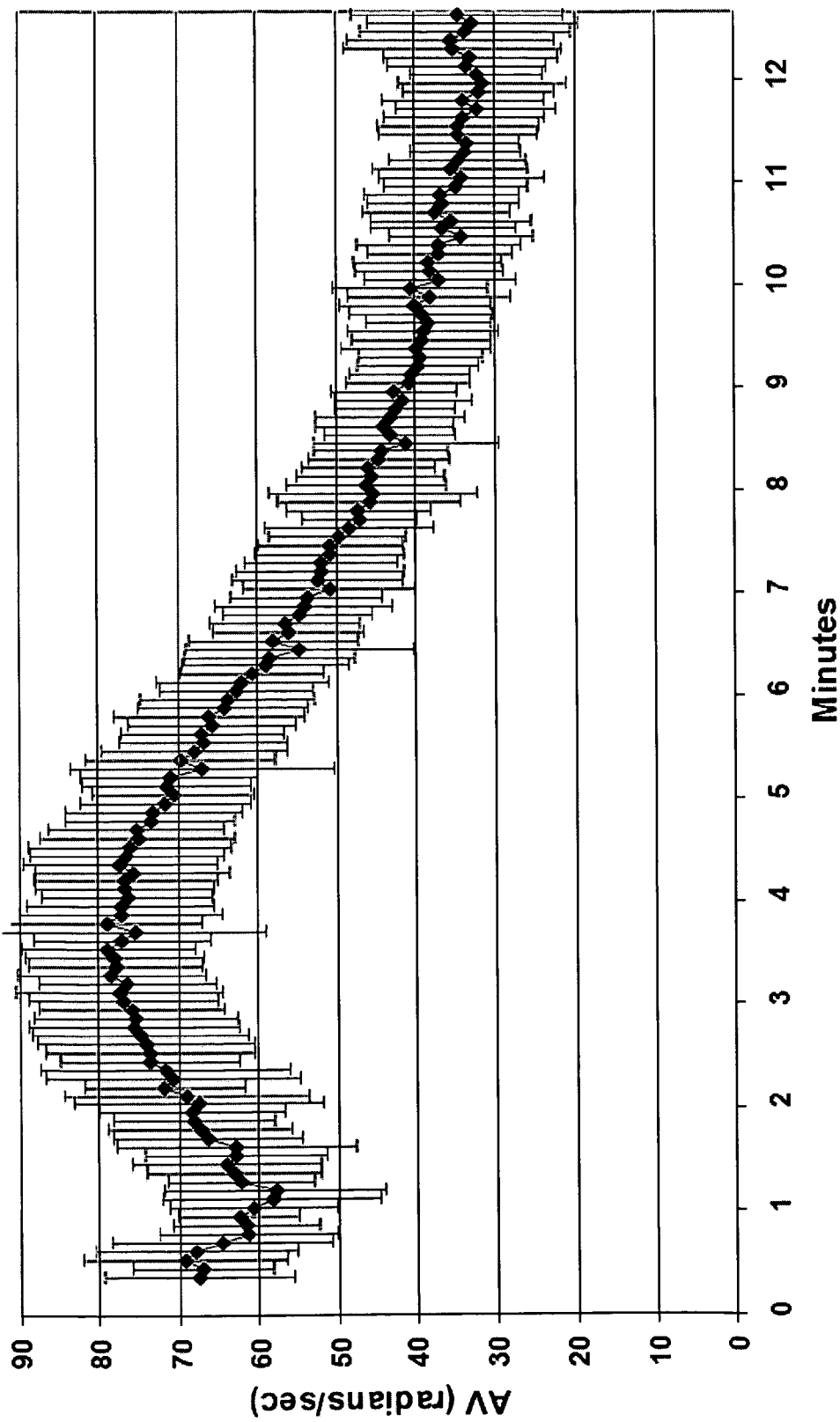
FIG. 6 illustrates a plot of the angular velocity as a function of time during ventricular fibrillation for a lag of 10.

Results of angular velocity calculated for 45 swine are shown in FIG. 6. As illustrated in FIG. 6, there was a clear overall decrease in average angular velocity over 12.5 minutes of VF. From 60 seconds of VF there was a gradual increase in the angular velocity from 58 rad/sec until 4 minutes, when it reached a value of 79 rad/sec. From this point forward in time, the angular velocity decreased steadily to 32 rad/sec at 12.5 minutes. The curve was thus multiphasic. Standard deviation for each point is shown in FIG. 6.

Probability Density Estimates

Computer software programs written in C++ were used to estimate the probability density for AV and ScE values from all 5 second epochs from VF recordings of less than 5 minutes duration. This procedure was then repeated for all values from epochs of VF from 5 to 12.5 minutes. Probability density estimates were based on the kernel density estimator technique. See Williams, G P, *Chaos Theory Tamed*, Washington, D.C.: Joseph Henry Press; p. 74-5, 1997, the disclosure of which is incorporated herein by reference. For each recording of VF, the ScE and AV were calculated from the onset of VF recorded at 1000 samples/sec to the first intervention performed. Each calculation was performed on 5000 samples, or 5 seconds of recorded data, and these were done on consecutive epochs until the end of the recording for each animal. For a full 12.5 minutes of recording there would be a total of 150 5-second epochs of data. These calculations were performed for all 45 recordings. There were 4847 such 5-second epochs. Of these, 2047 were from VF of less than 5 minutes duration, and 2800 were from VF of greater than 5 minutes duration. Each epoch was regarded as a data point and had individual ScE and AV values associated with it. By plotting the points in two dimensions, with the ScE along the abscissa and the AV along the ordinate, a two-dimensional "scattergram" of the points was formed. These two groups of points were then placed on the two-dimensional plot. A tent map kernel was employed using a bin width of 0.02, and density estimates were performed at intersections of a lattice grid from 1.00 to 1.40, with a spacing of 0.02 on the abscissa for ScE, and from 0 to 0.10, with a spacing of 0.005 on the ordinate for AV. A bin radius of 0.02 was used. At each point in the lattice all points in the sample were tested to see if they would fall within the bin radius. If the point was within the radius it was weighted according to its distance from the lattice point according to the tent map kernel formula: 1-distance from lattice point/radius. The weighted values of all points falling within the radius were summed and then the sum was divided by the total number of points in the sample and again divided by the radius to give the probability density estimate at that lattice point. This calculation was done for each of the 441 lattice points. The resulting two-dimensional probability density estimate was then plotted on a surface/mesh plot in MATLAB (Release 12, version 6.0.0.88, 2000, available from Mathworks, Inc.). Taking all points under 5 minutes and calculating the probability density distribution produced a characteristic picture of the probability that the points in this time range would fall in a particular region of the two-dimensional plot. This procedure was then repeated for all points from 5 to 12.5 minutes.

Figure 7:
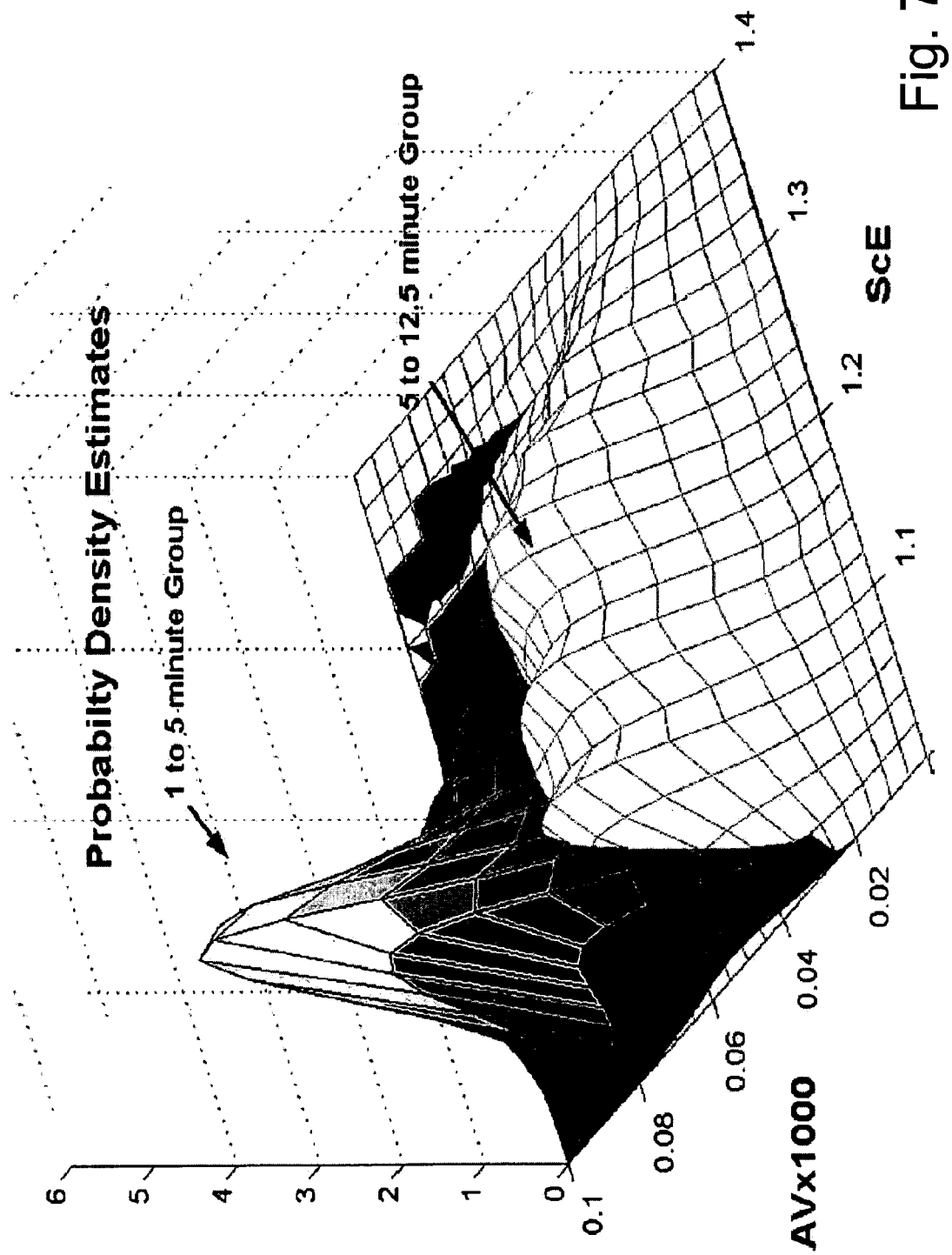
FIG. 7 illustrates a probability density estimate surface plot over a range of angular velocity and scaling exponent.

The surface plots of the two groups of VF is illustrated in FIG. 7 and exhibited a higher peak in the less than 5 minute group as a result of the concentration of these values centered around the ScE of 1.07 and an AV of 70 rad/sec values. The group of points greater than 5 minutes exhibited a lower peak but includes an equal volume. When these two plots were combined, there was a relative minimum (valley) between the two peaks which represented the line where the probability of the points being from one group or the other is equal. This was taken as the classification line for separating the two classes of points. This line was then approximated using a third-degree polynomial using the polyfit function of MATLAB. The "valley" between the peaks followed a line which was increasing initially in the direction of both ScE and AV, but then showed no increase in the AV direction.

Figure 8:
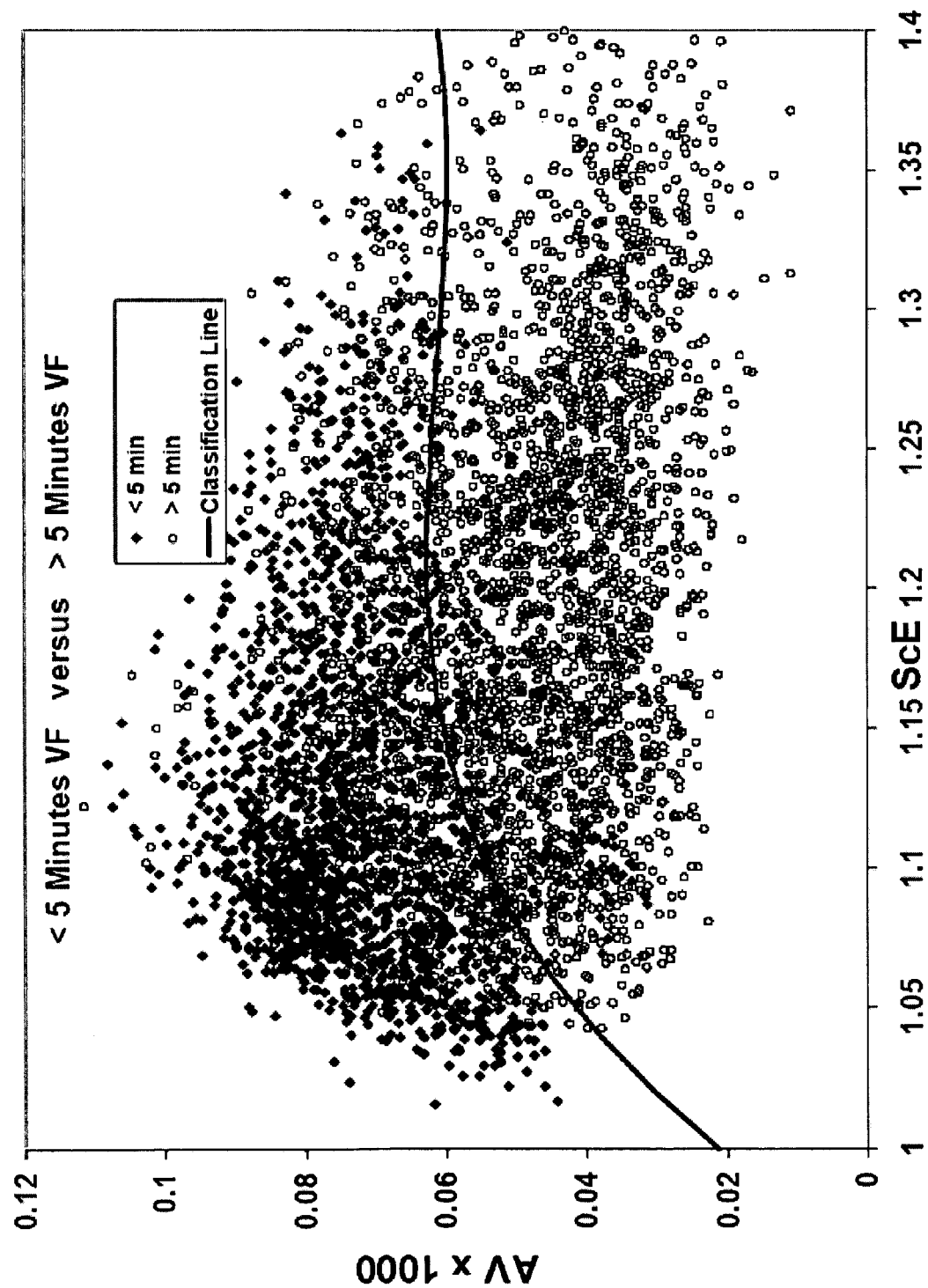
FIG. 8 illustrates a two-dimensional scattergram of angular velocity and scaling exponent with a fitted classification line for use in classifying an associated waveform as corresponding to ventricular fibrillation duration of less than or greater than 5 minutes.

The classification line between the two groups of VF is illustrated in FIG. 8. To determine how effective this classification line was at discriminating between the two groups, all points in the 0-5 minute group were tested with software programs written in C++ to determine how many fell outside of the 0-5 min region set off by the classification line. The ScE was calculated for each epoch and the value of the classification line at that ScE was then calculated. If the AV value for that point was greater than the value of the classification line, it was in the "less than 5 minutes duration" VF group, otherwise it was a misclassification. The 5-12.5 minute group was similarly tested for misclassification. By considering the less than 5 min duration VF group as the group with the "disease process" under consideration, a 2×2 table was developed to summarize the sensitivity, specificity, positive predictive value and negative predictive values of the test.

The presence of ventricular fibrillation of a duration less than 5 minutes was taken as the "disease" to be identified by the test. The results are shown in FIG. 9. The sensitivity was 90.4%, expressing the fact that a high percentage of recordings of ventricular fibrillation of less than 5 minutes are identified with this strategy. Also, the negative predictive value of 91.4% demonstrated that if the test value was ventricular fibrillation of greater than 5 minutes, then there is a high probability that the time frame from which it is taken is actually over 5 minutes.

As described above, the ScE is a quantitative estimate of the roughness of the VF waveform and has proved useful in determining VF duration. One advantage of the ScE is that it is continuously rising. However, ScE does contain a plateau from 5 to 8 minutes, which potentially limits its value in predicting VF duration in this region. The two regions of rapid increase of ScE from 0 to 5 minutes and from 8 to 12.5 minutes provide significant determinative features.

Figure 10:
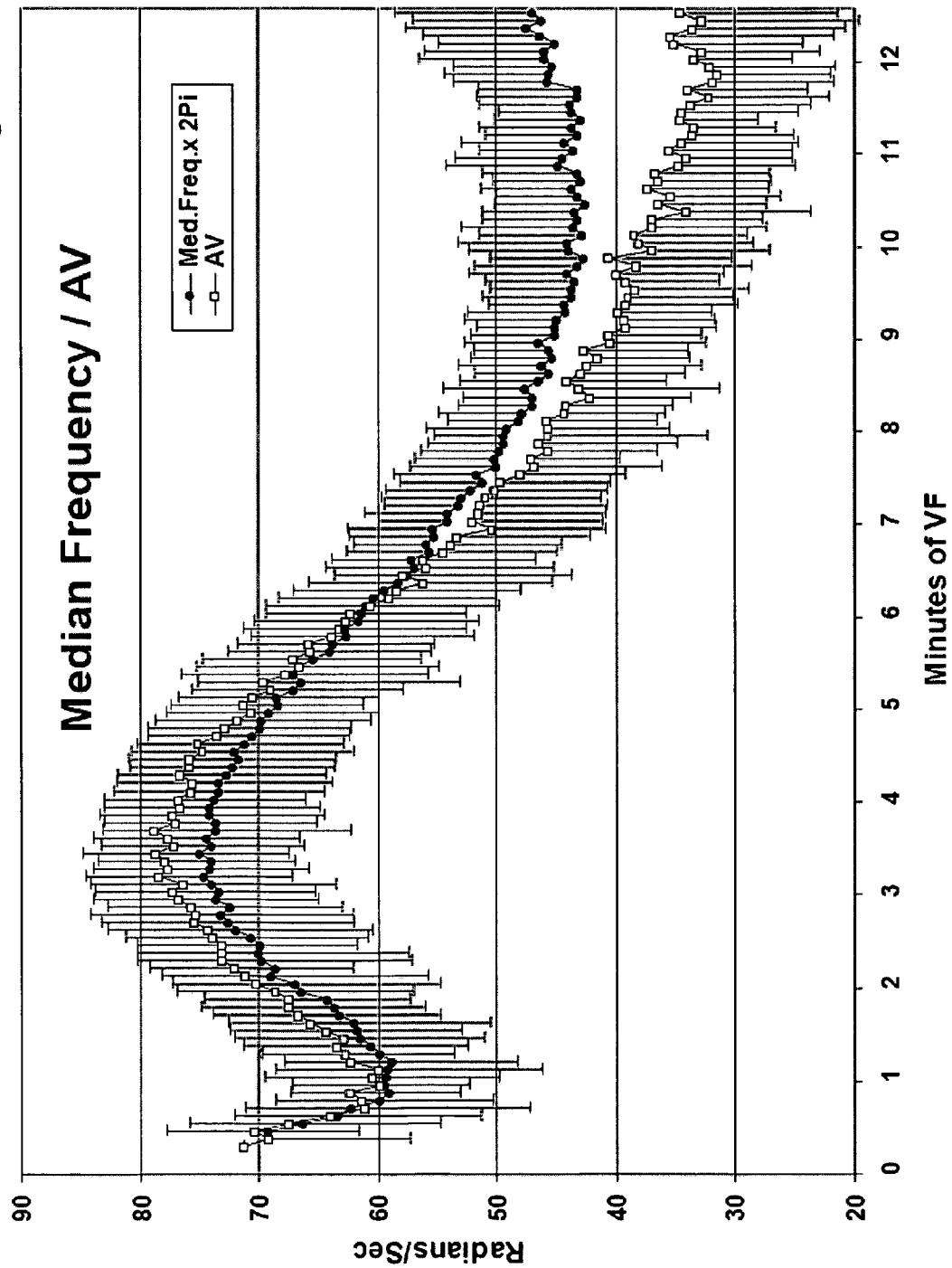
FIG. 10 illustrates a comparison of the median frequency to angular velocity as a function of time during ventricular fibrillation.

Angular velocity calculations of the present invention provide valuable predictive information in regions of VF in which the ScE is limited (that is, the 5-8 minute plateau region). Angular velocity calculations demonstrate a correlation with time which, in several respects, is similar to the median frequency measure. The AV measures an average of the number of rotations in a 5-second epoch. Each rotation may be viewed as a wave when seen in phase space (just as the sine wave produces a complete rotation over $2\pi$ radians). Hence the AV can be viewed as a "frequency based" measure. Like the median frequency, it is multiphasic. There is an initial dip and then an increase from 58 rad/sec at 1 minute to 79 rad/sec at 4 minutes, followed by a linear decline to 32 rad/sec at 12.5 minutes. A comparison of AV with median frequency for the same 45 recordings is illustrated in FIG. 10. To directly compare the measures, the median frequency values were multiplied by $2\pi$, which converted those values to radians per second. In FIG. 10, it is seen that the median frequency has a tendency to rise at later time periods while the AV continues to decrease. The median frequency is a frequency-based measure derived from Fourier transform calculations and may be more sensitive to noise in the sample at later times. Because AV does not begin to rise at later time periods in the same manner as the median frequency, it provides a clear advantage over median frequency in determining the duration of VF or the state of VF at such later time periods or states associated therewith.

The combination of ScE and AV in several embodiments of the present invention improves the accuracy of VF duration estimates and provides an improved method of characterization of the VF waveform, to, for example, identify states of the waveform and to identify preferred or optimal treatment methodologies associated therewith. The measured ScE and AV are substantially independent of body habitus, electrode position, electrode conductance, myocardial mass, etc. The ability to predict the probability of success of defibrillation (as, for example, represented by the ability to distinguish VF of less than 5 minutes duration from and VF of greater than 5 minutes duration) is, for example, a significant advance in the art. Moreover, it is expected that VF states associated with later time periods will be distinguishable using these and related techniques of the present invention. This ability allows therapies to be developed which can focus on the different states of VF. Such states have, for example, been divided into the electrical, the circulatory and the metabolic "phases". See, for example, Weisfeldt, M L, and Becker, L B, "Resuscitation after cardiac arrest: a 3-phase time-sensitive model," *JAMA*, 288(23), 3035-8, 2002. Furthermore, the ScE has been shown to be predictive of the probability of successful response to defibrillation attempts in humans. A combination of the ScE and AV can improve on this predictive ability. The effect of therapies on the myocardium and hence on the VF waveform may be reflected by changes in the ScE and AV so that the timing of defibrillation attempts could be based specifically on the changes in these measures as a response to interventions.

The decrease in angular velocity over time also supports the possibility that this statistic is a measure of the underlying physiology of the myocardium. The decrease in angular velocity over time is consistent with the hypothesis that the reduction in energy stores over time results in a slowing of conduction velocity, which is then reflected in the slowing of rotational velocity.

Figure 11:
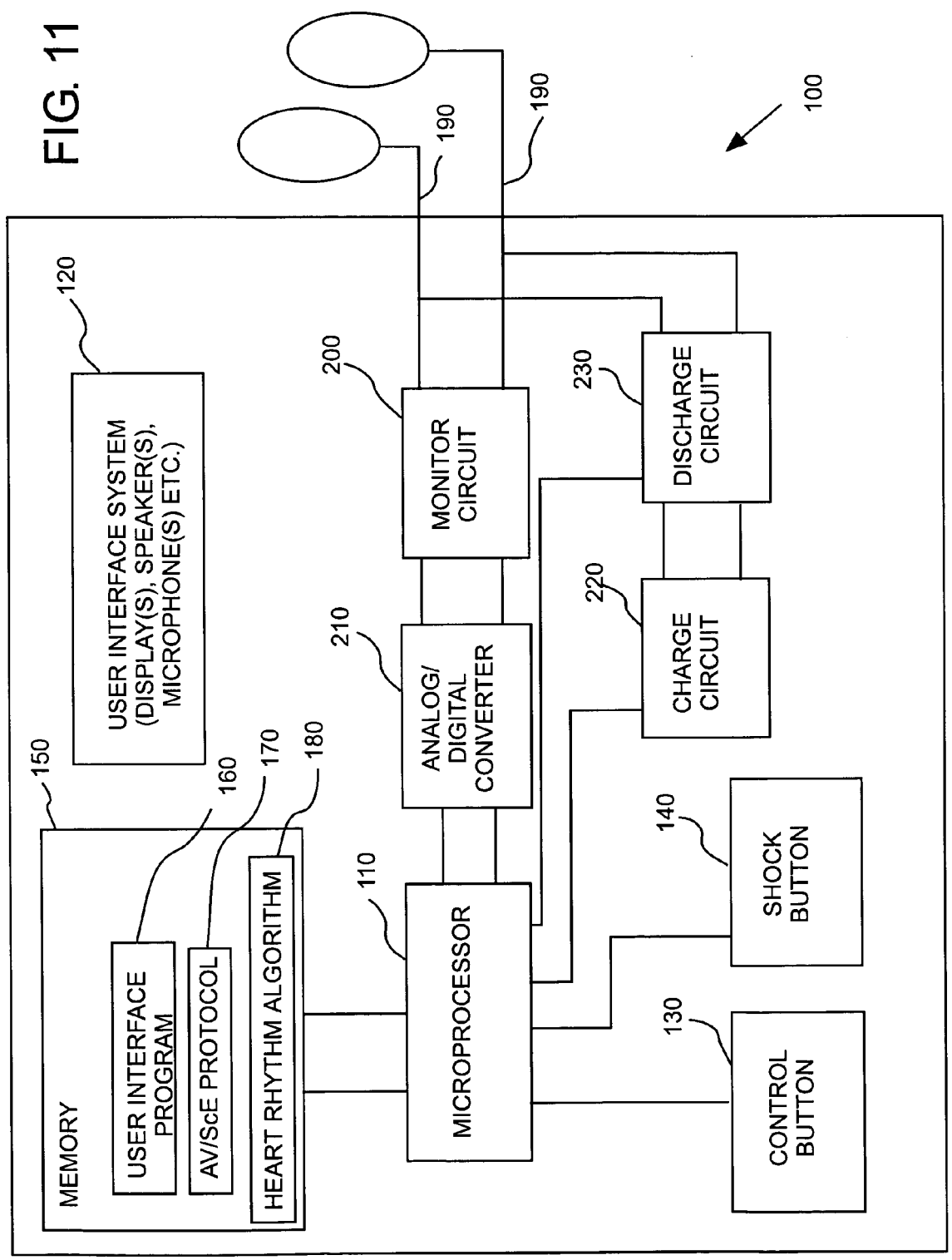
FIG. 11 illustrates an embodiment of an automated external defibrillator of the present invention incorporating a protocol or tool to determine the duration of ventricular fibrillation.

A treatment methodology, protocol or tool of the present invention (such as illustrated in FIGS. 7-9) can readily be incorporated into an existing defibrillator as illustrated in FIG. 11. In that regard, FIG. 11 illustrates schematically an embodiment of an automated external defibrillator (AED) similar to that disclosed in U.S. Pat. No. 6,697,671, the disclosure of which is incorporated herein by reference. Another example, of an AED into which the protocols of the present invention can be incorporated is disclosed in U.S. Pat. No. 6,662,046, the disclosure of which is incorporated herein by reference. Commercially available AEDs into which the protocols of the present invention can be incorporated include the LIFEPAK® series of AEDs available from Medtronic Physio-Control Manufacturing Corp. of Redmond Wash. Although those AEDs are set forth as representative examples of defibrillators into which the protocols of the present invention can be incorporated, one of ordinary skill in the art appreciates that such protocols can be incorporated into virtually any device or system in which heart rhythm is measured.

AED 100 includes a processor (a microprocessor 110 in the illustrated embodiment) which generally controls the operation of the AED 100. The processor used can, for example, be an analog processor or a digital processor, and suitable processors include, but are not limited to: microprocessors, workstations, PC's, hardwired circuitry and the like. Microprocessor 110 is in communicative connection with a user interface system 120, which can include one or more of each of a display, a microphone, a speaker, etc. for the input or output of information. A start/control button 130 and a shock button 140 can also be in operative connection with microprocessor 110.

A memory 150 including a user interface program 160 stored therein is also in communicative connection with microprocessor 110. Memory 150 also has stored therein, for example, as part of or in operative communication with user interface program 160, an operation protocol or program 170 based upon angular velocity/angular area or based upon angular velocity/angular area and the scaling exponent as described above. User interface program 160 can, for example, be formatted as described generally in U.S. Pat. No. 6,697,671. User interface program 160 can, for example, generate visual instructions upon a display of user interface system 120 and/or generate audible instructions transmitted via one or more speakers of user interface system 120. Memory 150 can additionally store a voice recognition software module as known in the art, to enable a user to operate AED 100 and respond to visual and/or audible instructions via voice command rather than using control buttons such as start button 130 and shock button 140.

During operation, the microprocessor 110 analyzes an electrocardiogram (ECG) of a patient using, for example, an automatic heart rhythm algorithm 180 such as disclosed in U.S. Pat. No. 6,697,671 or other algorithm, which is stored in memory 150 to track the heart rhythm of the patient. Currently, such algorithms are functional, for example, to identify whether the patient is experiencing a shockable heart rhythm, such as ventricular fibrillation. Such algorithms are used, for example, in the LIFEPAK® 500 defibrillator available from Medtronic Physio-Control Corp. Other such algorithms include those designed to comply with standards promulgated by the Association for the Advancement of Medical Instruments (AAMI). ECG signals analyzed by heart rhythm algorithm 180 are collected by the electrodes 190 and communicated through monitor circuit 200 to an analog-to-digital converter 210, which then passes the digitized signals to microprocessor 110. Under current practice as described, for example, in U.S. Pat. No. 6,697,671, if microprocessor 110 detects a shockable rhythm, microprocessor 110 causes a charging circuit 220 to generate a current causing a storage capacitor (not shown) to charge in preparation for delivery of a defibrillation pulse to the patient. When the capacitor is fully charged, and delivery of the defibrillation pulse is initiated, a discharge circuit 230 in operative communication with microprocessor 110 and charge circuit 220 discharges the defibrillation pulse to electrodes 190 for application of the defibrillation pulse to the patient.

The present invention provides a significant advance in the art by providing operation protocol 170 (which can, for example, operate in conjunction with heart rhythm algorithm 180), based upon angular velocity/angular area or based upon angular velocity/angular area and the scaling exponent as described above. In accordance with the procedures described above, such an operation protocol can be used to characterize the ventricular fibrillation waveform and/or to determine the state of ventricular fibrillation. The determined character or state of the ventricular fibrillation waveform can be used to determine a likelihood of success of defibrillation to, for example, cause AED 100 to automatically deliver a defibrillation pulse if the determined probability is greater than a defined threshold or to prevent delivery of a defibrillation pulse by AED 100 or to warn against shocking if the probability of success of defibrillation shock is less than a defined threshold. If the success of defibrillation shock is determined to be less than a defined threshold, then the AED can also advise the rescuer to begin CPR or an alterative treatment rather than to shock.

When used in connection with monitor/defibrillators such as used by highly trained individuals, the treatment protocol of the present invention can provide information as to the character or state of ventricular fibrillation waveform to allow, for example, a physician to determine a proper treatment associated with that character or phase. If, for example, the state of ventricular fibrillation is consistent with the circulatory phase (as described by Weisfeldt and Becker) then a period of CPR may be performed. If the ventricular fibrillation is consistent with the metabolic phase, then the advanced life support caregivers can acquire intravenous access and give drugs needed to improve the metabolic state of the heart prior to defibrillation. The defibrillator system can also recommend a treatment based on the probability of a shock (or other treatment) being successful. A recommended treatment or therapy other than defibrillation (should the probability of success of defibrillation be determined by the system to be below a threshold value) can include, but is not limited to: (1) reperfusion; (2) reoxygenating the fibrillating heart of the patient; (3) employing a period of cardiopulmonary resuscitation (CPR) (4) employing artificial perfusion; (5) employing one or both of CPR and ventilating the patient and (6) drug administration. Such alternative therapies can be followed by defibrillation, the application and timing of which can be recommended by the system of the present invention based, for example, upon the likelihood of success thereof.

Figure 12A:
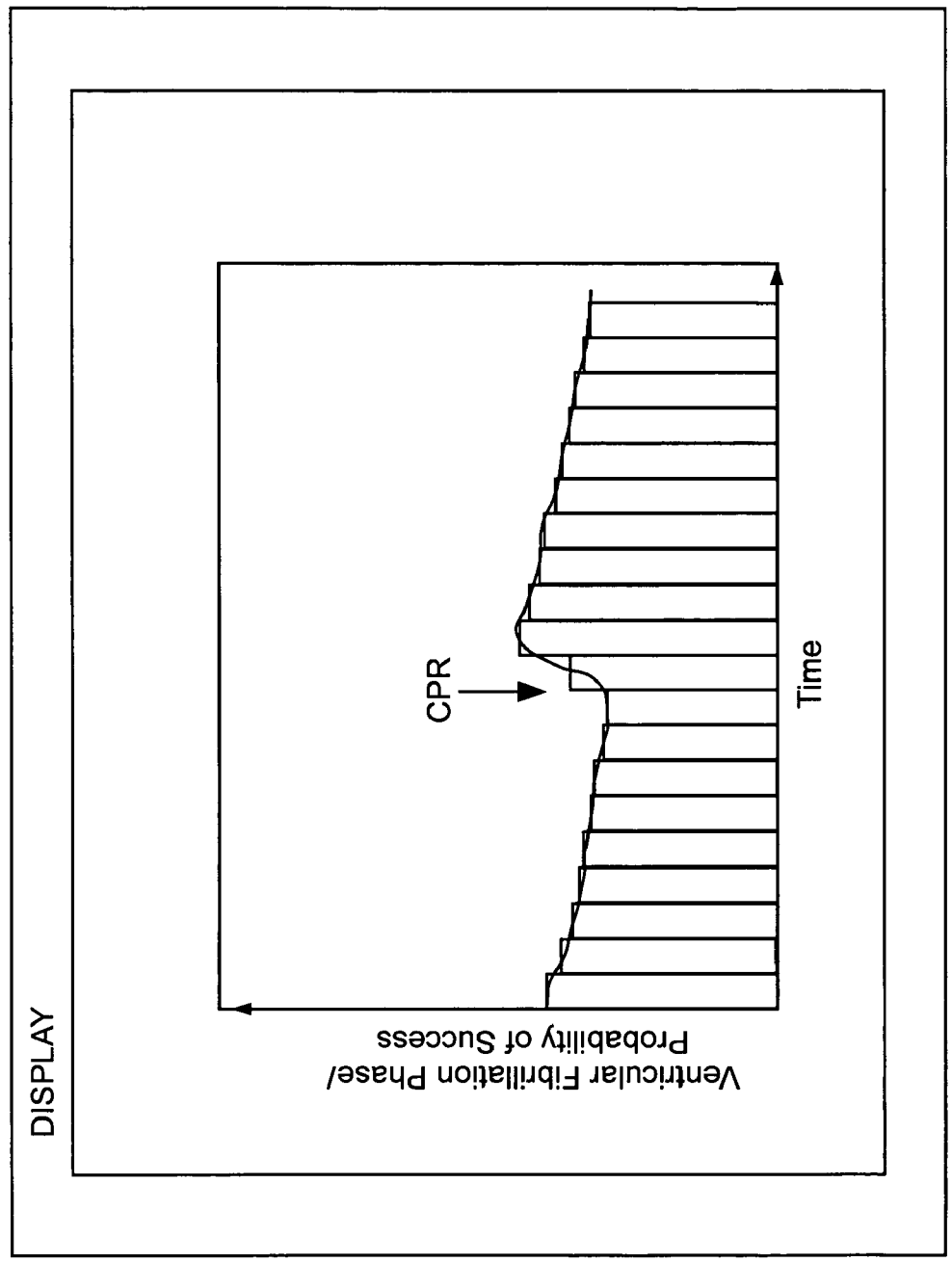
FIG. 12A illustrates an embodiment of a display of the present invention setting forth a measure of the character or state of a ventricular waveform as a function of time and the probability of success of a treatment for ventricular fibrillation as a function of time.
Figure 12B:
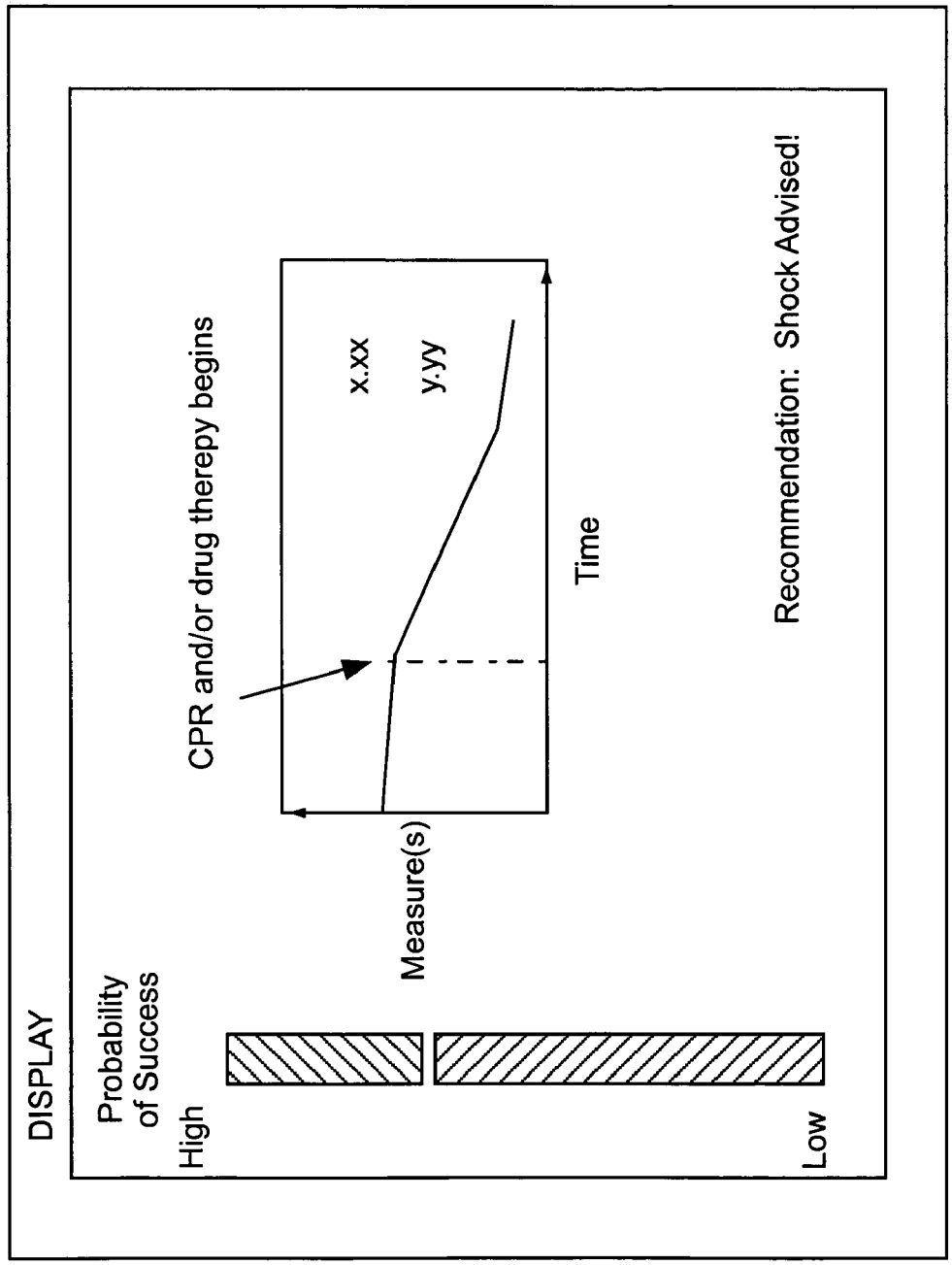
FIG. 12B illustrates another embodiment of a display of the present invention setting forth a measure of the state of ventricular waveform as a function of time and the probability of success of a defibrillation shock.

For experienced users, the output of the algorithm can be indicated by a continuous indicator related to the likelihood of a success of a treatment such as defibrillation to allow determination if a shock should be applied to the patient. The continuous indication can, for example, take forms including, but not limited to, a numeric probability, a continuous gauge or indicator such as a "gas gauge" bar, a bar graph of probability (see FIGS. 12A and 12B) or a color-coded indicator. For experienced users, the time course of the character or state of the VF waveform of the calculated probability of success of a treatment can also be plotted to indicate the progression of the patient's cardiac condition, and to track the response to interventions such as medications or CPR (see FIGS. 12A and 12B). Indeed, interventions such as CPR are know to change the character or state of the ventricular fibrillation waveform and increase the likelihood of success of a defibrillation shock. Using duration of ventricular fibrillation as a model of changing waveform character or state, application of CPR can have the effect of slowing the rate change of the waveform character or even the effect of taking the character or state of the waveform back in time. The angular velocity/angular area and scaling exponent variable can accurately track the change in the character or state of the ventricular fibrillation waveform before, during and after such intervention(s). Experienced users may use these trends to determine when to start or stop particular interventions, and when or whether to apply a defibrillation shock. In FIG. 12A, for example, the character of the VF waveform and the probability of success of defibrillation shock (plotted as bars) as determined by the average angular velocity and the scaling exponent is plotted as a function of time. As illustrate in FIG. 12A, the application of CPR (or other therapy) during VF changes the character of phase of the VF waveform and increases the probability of success of defibrillation shock. FIG. 12B illustrates another embodiment of a display of the present invention in which one or more measures of VF waveform state of the present invention (for example, angular velocity, angular area and/or scaling exponent) are displayed continuously in graphical form and as in numeric form (represented by x.xx and y.yy in FIG. 12B). A real time bar gauge of the probability of success of a defibrillation shock is also set forth.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A method of determining a state of ventricular fibrillation, comprising;
   measuring the rhythm of the heart during ventricular fibrillation for a period of time;
   creating a lagged phase space reconstruction of the measured ventricular fibrillation heart rhythm using a constant time lag;
   determining a first value related to the rate of change of the leading edge of the lagged phase space reconstruction over the period of time; and
   determining the state of ventricular fibrillation based upon the determined first value to determine a treatment.

2. The method of claim 1 wherein the first value is average angular velocity for the period or angular area for the period.

3. The method of claim 2 wherein the average angular velocity for the period of time is the rate of rotation of the leading edge of the lagged phase space reconstruction about the center of mass of points at an average rate.

4. The method of claim 1 wherein the lagged phase space reconstruction is a two-dimensional reconstruction.

5. The method of claim 1 wherein the lagged phase space reconstruction is a three-dimensional reconstruction.

6. The method of claim 1 further comprising: determining a second value related to the fractal self-similarity dimension of the ventricular fibrillation heart rhythm for the period of time, the step of determining the state of fibrillation including the step of relating at least one of the first value and the second value to the state of fibrillation.

7. The method of claim 6 wherein the second value is a scaling exponent.

8. The method of claim 7 wherein the first value is average angular velocity.

9. The method of claim 8 wherein the determined state of ventricular fibrillation is associated with a probability of success of a mode of treatment of ventricular fibrillation.

10. The method of claim 9 wherein the mode of treatment is defibrillation shock.

11. The method of claim 10 wherein the probability of success of the defibrillation shock is associated with the scaling exponent and the angular velocity.

12. A method of determining a treatment for a patient experiencing ventricular fibrillation, comprising:
   measuring the rhythm of the heart during ventricular fibrillation for a period of time;
   creating a lagged phase space reconstruction of the measured ventricular fibrillation heart rhythm using a constant time lag;
   determining a first value related to the rate of change of the leading edge of the lagged phase space reconstruction over the period of time to determine the treatment; and
   relating the first value to a treatment for the patient.

13. The method of claim 12 wherein the first value is average angular velocity for the period or angular area for the period.

14. The method of claim 13 wherein the average angular velocity is the rate of rotation of the leading edge of the lagged phase space reconstruction about the center of mass of points at an average rate.

15. The method of claim 12 wherein the lagged phase space reconstruction is a two-dimensional reconstruction.

16. The method of claim 12 wherein the lagged phase space reconstruction is a three-dimensional reconstruction.

17. The method of claim 12 further comprising: determining a second value related to the fractal self-similarity dimension of the ventricular fibrillation heart rhythm for the period of time, the step of determining the treatment including the step of relating at least one of the first value and the second value to the treatment.

18. The method of claim 17 wherein the second value is a scaling exponent.

19. The method of claim 18 wherein the first value is average angular velocity.

20. The method of claim 18 wherein the determination of the treatment comprises relating at least one of the first value and the second value to a probability of success of defibrillation shock.

21. The method of claim 20 wherein a determination of the probability of success of a defibrillation shock comprises the step of relating the angular velocity and the scaling exponent to the probability of success.

* * * * *